(12) United States Patent
Binner

(10) Patent No.: US 8,314,377 B2
(45) Date of Patent: Nov. 20, 2012

(54) DEVICE AND METHOD FOR DETECTING PLAQUE IN THE ORAL CAVITY

(75) Inventor: Curt Binner, Furlong, PA (US)

(73) Assignee: McNeil-PPC, Inc., Skillman, NJ (US)

(*) Notice: Subject to any disclaimer, the term of this patent is extended or adjusted under 35 U.S.C. 154(b) by 471 days.

(21) Appl. No.: 12/645,542

(22) Filed: Dec. 23, 2009

(65) Prior Publication Data

US 2011/0151409 A1 Jun. 23, 2011

(51) Int. Cl.
*G01J 1/42* (2006.01)
(52) U.S. Cl. ............... 250/208.2; 250/227.11; 356/318; 15/167.1; 433/215; 433/216
(58) Field of Classification Search ............... 433/29, 433/215, 216, 125, 142, 144, 31, 25, 27; 15/167.1, 167.2; 356/317, 318; 600/431, 600/248; 128/898; 607/88–93; 250/208.2, 250/227.11, 227.13, 216
See application file for complete search history.

(56) References Cited

U.S. PATENT DOCUMENTS

| | | | |
|---|---|---|---|
| 3,261,978 A | 7/1966 | Brenman | |
| 3,309,274 A | 3/1967 | Brilliant | |
| 3,711,700 A | 1/1973 | Westlund et al. | |
| 3,732,416 A | 5/1973 | Audesse et al. | |
| 5,382,163 A | 1/1995 | Putnam | |
| 5,894,620 A | 4/1999 | Polaert et al. | |
| 5,957,687 A | 9/1999 | Brilliant | |
| 6,024,562 A | 2/2000 | Hibst et al. | |
| 6,053,731 A | 4/2000 | Heckenberger | |
| 6,485,300 B1 | 11/2002 | Muller et al. | |
| 6,561,808 B2 | 5/2003 | Neuberger | |
| 6,616,451 B1 | 9/2003 | Rizolu et al. | |
| 6,862,771 B1 | 3/2005 | Muller | |
| 6,902,397 B2 | 6/2005 | Farrell et al. | |
| 7,223,270 B2 | 5/2007 | Altshuler et al. | |
| 7,324,661 B2 | 1/2008 | Kemp et al. | |
| 7,328,708 B2 | 2/2008 | Malak | |
| 7,329,273 B2 | 2/2008 | Altshuler et al. | |

(Continued)

FOREIGN PATENT DOCUMENTS

| | | |
|---|---|---|
| WO | WO 92/06671 | 4/1992 |
| WO | WO 97/29714 | 8/1997 |
| WO | WO 2004/084752 A | 10/2004 |
| WO | WO 2006/047868 A | 5/2006 |
| WO | WO 2006/098719 A | 9/2006 |
| WO | WO 2007/111703 A | 10/2007 |
| WO | WO 2008/059435 A | 5/2008 |
| WO | WO 2008/088241 A | 7/2008 |
| WO | WO 2009/070344 A | 6/2009 |
| WO | WO 2009/134784 A | 11/2009 |

OTHER PUBLICATIONS

Sagel et al, "Objective Quantification of Plaque Using Digital Image Analysis", Faller RV (ed): Assessment of Oral Health, Monogr Oral Sci. Basel, Karger, 2000, vol. 17, pp. 130-143.

*Primary Examiner* — Francis M Legasse, Jr.

(57) ABSTRACT

The present invention regards methods and devices for detecting plaque on a surface in the oral cavity to which a fluorescent agent capable of binding to plaque has been applied, whereby a radiation source emits incident radiation for contacting the surface, reflected light and fluorescent emission resulting from contact of the radiation with the surface is collected by an optical collector and conveyed by an optical pathway in the device, where the optical light signal of the reflected light and fluorescent emission is converted to an electrical signal, and where the electrical signals of the fluorescent emission and the reflected light are then mathematically manipulated to provide a compensated plaque value as a function of the distance from the optical collector and the surface of the oral cavity to which the fluorescent agent has been applied.

23 Claims, 2 Drawing Sheets

U.S. PATENT DOCUMENTS

| | | |
|---|---|---|
| 2003/0156788 A1 | 8/2003 | Henning |
| 2004/0023184 A1 | 2/2004 | de Josselin de Jong et al. |
| 2004/0106081 A1 | 6/2004 | Karazivan et al. |
| 2005/0053898 A1 | 3/2005 | Ghosh et al. |
| 2005/0170316 A1 | 8/2005 | Russell et al. |
| 2006/0085052 A1 | 4/2006 | Feuerstein et al. |
| 2006/0141421 A1 | 6/2006 | Braunecker et al. |
| 2006/0183071 A1 | 8/2006 | Hsuch |
| 2006/0257822 A1 | 11/2006 | Ghosh et al. |
| 2007/0038272 A1 | 2/2007 | Liu |
| 2007/0111166 A1 | 5/2007 | Dursi |
| 2007/0111167 A1 | 5/2007 | Russell et al. |
| 2007/0280888 A1 * | 12/2007 | Fujikawa et al. ............ 424/9.71 |
| 2007/0298372 A1 | 12/2007 | Pinyayev et al. |
| 2008/0060148 A1 | 3/2008 | Pinyayev et al. |

* cited by examiner

DEVICE AND METHOD FOR DETECTING PLAQUE IN THE ORAL CAVITY

FIELD OF THE INVENTION

This invention relates to devices and methods for detecting plaque on a surface in the oral cavity, e.g. teeth and gums, which surface has been treated with a fluorescent agent that binds to plaque and for determining a compensated plaque value.

BACKGROUND OF THE INVENTION

Biological deposits generally refer to deposits of material of biological origin, such as plaque, bacteria, tartar, and calculus that are generally regarded as undesirable for dental hygiene. Dental plaque is a complex organic deposit generated in part by the activity of bacteria upon surfaces of the oral cavity, such as on the teeth, or upon contamination from, for example, food deposits on the teeth, gums, tongue, or cheek. Plaque is an undesirable precursor to tooth decay, periodontal disease and the development of dental caries.

It is desirable to detect plaque deposits in the oral cavity before removing them, for example by using toothbrushes (manual or power), tooth floss, tooth picks, or oral irrigators, as detection indicates the areas at which dental cleaning effort should be focused. Such deposits may be difficult to detect in situ/in vivo on the teeth, gums, tongue, or cheek. It is especially important to detect dental plaque. For detection of plaque it is known to use fluorescence measurement, in which incident radiation is directed at the surfaces of the oral cavity, and fluorescence radiation having characteristics associated with the presence of biological deposits is emitted from the surfaces and is detected.

In the state of the art there are two general methods for detecting dental plaque, using respectively primary fluorescence in which the fluorescence of dental plaque or other dental material itself is monitored, and secondary fluorescence in which surfaces in the oral cavity suspected of bearing plaque are treated with a fluorescent label material which preferentially binds to dental plaque, and the fluorescence emission of the label material on the oral cavity surfaces at which it has bound is detected to indicate the presence of dental plaque. Also know are toothbrush heads having a bundle of optical fibers extending through it to direct incident radiation at a test tooth surface, and to collect emitted radiation from the test tooth surface.

A requirement of such methods is that incident radiation is directed at the surfaces of the oral cavity under examination and that consequent fluorescence emission radiation from those surfaces is collected. The amplitude of that radiation is a function of the amount of biological deposit located on the surface, as well as the distance the light source and detectors are from the surface. Consequently, the actual plaque value detected will fluctuate depending upon such factors, thereby resulting in a plaque value which may not truly depict the condition of plaque on the surface of the oral cavity. Known devices are not known to compensate for distances between the source of radiation and/or sensors and the surface of the oral cavity when determining the amount of biological deposit on the oral cavity surfaces.

Devices and methods for detecting plaque in the oral cavity according to the invention described and claimed herein compensate for the distance between the source and/or optical sensors of the incident radiation and on the oral cavity surface being examined, thus providing a compensated plaque value.

SUMMARY OF THE INVENTION

Methods for detecting plaque in the oral cavity according to the present invention include contacting a surface of the oral cavity with incident radiation, where the surface being contacted comprises applied thereto a fluorescent agent capable of binding to plaque. Contacting the surface with the incident radiation provides reflected light having a first peak wavelength and a fluorescent emission having a second peak wavelength emanating from the fluorescent agent. A first portion of the fluorescent emission resulting from the contact is collected by a first optical collector and conveyed by an optical pathway to a first means for converting an optical light signal of the first fluorescent emission to an electrical signal of the first portion of fluorescent emission, where the optical light signal of the first portion of fluorescent emission is converted to the electrical signal of the first portion of the fluorescent emission. A first portion of the reflected light is collected by a second optical collector and conveyed to a second means for converting an optical light signal of the first portion of the reflected light to an electrical signal of the first portion of the reflected light, where the optical light signal of the first portion of the reflected light is converted to the electrical signal of the first portion of the reflected light. The electrical signals of the first portion of the fluorescent emission and the first portion of the reflected light are then mathematically manipulated to provide a compensated plaque value, as that term is defined and described herein below.

The invention also is directed to devices for detecting plaque on the surface of the oral cavity to which a fluorescent agent has been applied, such devices include a radiation source for directing incident radiation onto the surface of the oral cavity, first and second optical collectors for collecting reflected light and fluorescent emission, optical pathways for conveying reflected light and fluorescent emission in the device, means for converting the optical light signal of the reflected light and fluorescent emission to an electrical signal, and means for mathematically manipulating the electrical signals to determine a compensated plaque value, as that term is described and defined herein below.

DETAILED DESCRIPTION OF THE INVENTION

Figure 1:
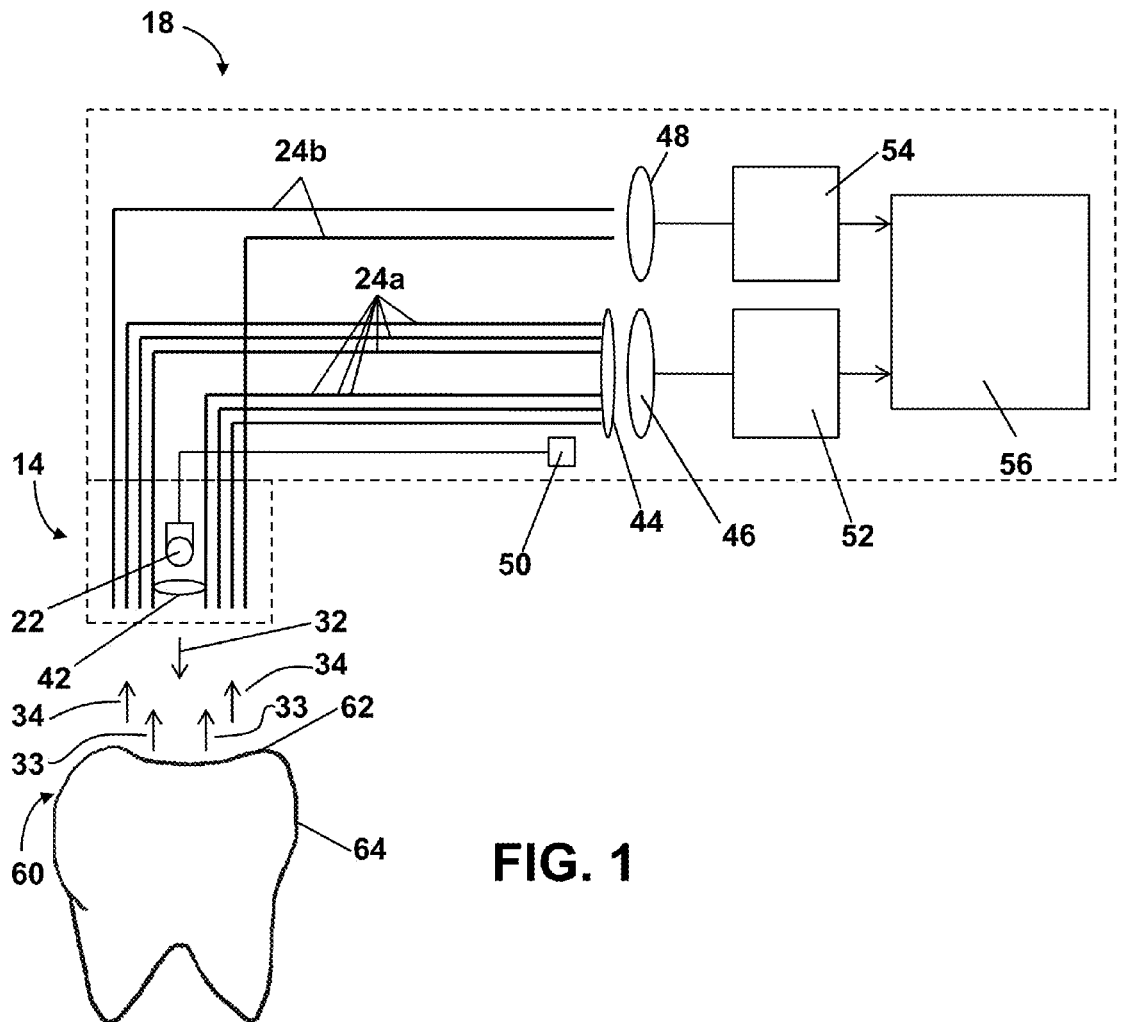
FIG. 1 is a schematic diagram of the operating principle of the plaque detecting device and methods of the present invention.

A device and methods for detecting plaque on the surface of the oral cavity are provided. The device comprises a radiation source for directing incident radiation onto a surface within the oral cavity. The radiation source typically may provide light having a peak wavelength of from about 450 to about 500 nanometers, although the range may vary depended upon the particular fluorescent agent applied to the surface of the oral cavity to be examined. The device may optionally include a filter for filtering incident radiation prior to contact with the surface of the oral cavity to be examined. The device also includes optical collectors for collecting reflected light and fluorescent emission resulting from contact of the incident radiation with the surface. In certain embodiments, the optical collectors may comprise optical fibers or filaments. The device also includes an optical pathway for conveying the collected reflected light and fluorescent emission in the device. In certain embodiments, the optical pathway may comprise optical fibers. As such, optical fibers may serve both to collect and convey the reflected light and fluorescent emission.

The device further includes electrical components for sensing the optical light signal of the reflective light and the fluorescent emission. In one embodiment, the optical light signals of the reflective light and the fluorescent emission are sensed, or detected, sequentially, but essentially simultaneously. By essentially simultaneously, it is meant that, while measurements are not taken exactly at the same time, the difference in time between detecting the reflective light and fluorescent light, respectively, is so small that the detection of each approximates the simultaneous reading. The device further comprises means for converting an optical light signal to an electrical signal, for example, a transducer. The devices may include means for amplifying or conditioning the electrical signal, thus providing a smoother or averaged signal, or a signal with reduced noise. The device also includes a data processor which may contain an analogue-to-digital converter for converting the electrical signal from an analogue format to a digital format. The processor then mathematically manipulates the electrical signal of the collected reflected light and fluorescent emission taken over iterative internals so as to determine a compensated plaque value. The value of the collected fluorescent emission is compensated, taking into account the distance between the optical collector and the surface of the oral cavity being examined. As such, the plaque value is determined as a function of the distance between the optical collector and the surface of the oral cavity at any given moment/reading. As a result of determining plaque value as a function of distance, the compensated plaque value so determined will be substantially the same, irregardless of the actual distance between the radiation source and the surface of the oral cavity. By substantially the same, it is meant that the determined compensated plaque value at any given distance is statistically the same. The device may be used as a component of, or in combination with, oral cleaning devices such as toothbrushes (manual or power), tooth floss, tooth picks, or oral irrigators.

Methods of detecting plaque and plaque detecting devices of the present invention involve the use of a fluorescent agent that is capable of binding to plaque present on a surface in the oral cavity, e.g. teeth and gums. In addition, the fluorescent agent is capable of providing a fluorescent emission when irradiated with incident radiation of a particular wavelength. For example fluorescein or salts thereof, e.g. sodium fluorescein, are known fluorescent agents and may be dispersed in a suitable medium, such as toothpaste, a dental gel, or a rinse containing the fluorescent agent. The fluorescent agent can be applied either by first rinsing the oral cavity with the fluorescent agent or by applying the toothpaste or dental gel containing the fluorescent agent. The plaque on the surfaces of the oral cavity retains an amount of fluorescent agent that is proportionate to the amount of plaque on the surface. While fluorescein is one example of a fluorescent agent, other agents are known that will bind to plaque similar to fluorescein. The particular wavelength of the incident radiation used in methods and devices of the present invention will vary, depending on the particular fluorescent agent chosen.

Figure 2:
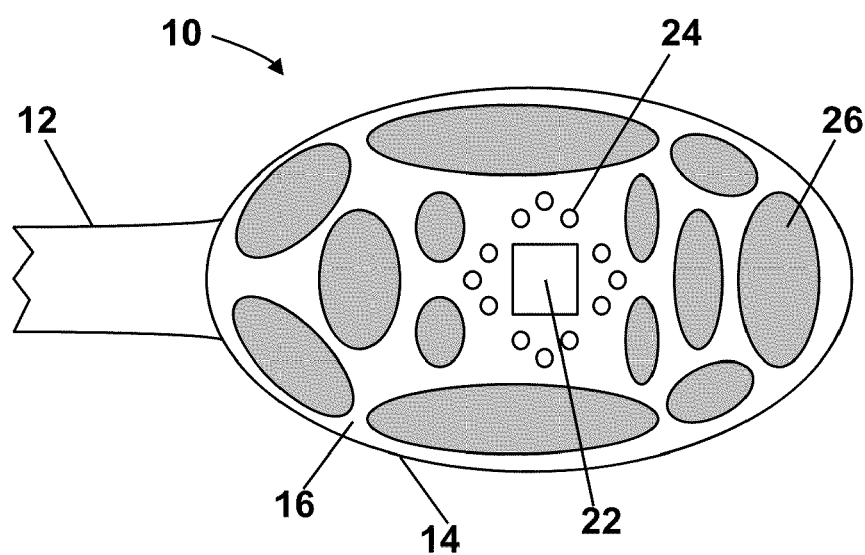
FIG. 2 shows a top plan view of an embodiment of the bristle face of a toothbrush head embodiment of the present invention.

FIG. 1 is a schematic diagram of the operating principle of methods and devices for detecting plaque according to the present invention. The particular embodiment represented is a toothbrush, although other devices for use within the oral cavity also are contemplated by the invention. FIG. 2 is a plan view of a toothbrush head according to the invention, taken from the bristle side of the brush head. In the embodiment shown, toothbrush head portion 14, represented as a first dashed box on FIG. 1, includes, in addition to conventional bristle tufts 26 for cleaning teeth, radiation source 22 and optical fibers 24a and 24b for conveying reflected light 33 and fluorescent emission 34 resulting from contact of the surface of the oral cavity with the incident radiation. Head 14 also may include first optical filter 42, depending on the radiation source.

Electrical housing 18, represented as a second dashed box in FIG. 1, will contain other electrical components of a plaque detecting device located therein, as described herein above. In some embodiments, electrical housing 18 may reside in a handle portion of the plaque detecting device, for example a toothbrush handle. In the embodiment shown, optical fibers 24a and 24b extend from head 14 into electrical housing 18. Housing 18 also includes contained therein, second optical filter 44, first optical transducer 46, second optical transducer 48, first amplifier 52, second amplifier 54, data processor 56 and power source 50 for operating the electrical components.

FIG. 1 also shows a representative surface of the oral cavity, e.g. tooth 60, with top surface 62 and side surface 64. Though FIG. 1 shows plaque detecting device 10 directed at top surface 62 of tooth 60, it is to be understood that both top surface 62 and side surface 64 of tooth 60, may be contacted with incident radiation. In addition, such contact may be simultaneously at top surface 62 and side surface 64 of multiple teeth 60, depending on the brushing technique of the user. The plaque detecting device may also be directed at other surfaces in the oral cavity, such as those of the gums, tongue, or cheek.

In operation, prior to use of the plaque detecting device, the oral cavity is treated with a fluorescent label material, i.e. a fluorescent agent, which preferentially binds to dental plaque and which produces a fluorescent emission when exposed to incident radiation. Depending on the particular fluorescent agent chosen, the peak wavelength of the incident radiation may vary. In embodiments utilizing fluorescein or salts thereof, e.g. sodium fluorescein, the incident radiation may have a peak wavelength ranging from about 450 to about 500 nanometers. Once placed within the oral cavity, radiation source 22 emits light at a peak wavelength of from about 450 to about 500 nanometers (nm), or about 470 nanometers. The light may be passed through first optical filter 42, which removes substantially all light having wavelength above about 510 nm. As shown, incident radiation 32 from radiation source 22 is directed at top surface 62 of tooth 60, although as discussed above, the incident radiation may contact multiple surfaces of the oral cavity, e.g. the teeth. Upon contact with the surface, incident radiation interacts with the fluorescent agent that has bonded to plaque located on the surfaces of tooth 60. The fluorescent agent then produces a fluorescent emission 34 having a peak wavelength of from about 520 to about 530 nanometers. A first portion of fluorescent emission 34 provided by the fluorescent agent is collected by optical fibers 24a and conveyed in the device by optical fibers 24a for further mathematical processing. Incidentally, a second portion of reflected light 33 is simultaneously collected and conveyed with the first portion of fluorescent emission 34. Fluorescent emission 34 is passed through a second optical filter 44, which removes substantially all light of wavelengths below about 515 nm, ensuring that essentially no reflected light is passed to the data processor 56. The now filtered fluorescent emission 34 passes through first optical transducer 46 in the form of a photodiode, which converts the optical light signal into an electrical signal. The electrical signal is passed through first amplifier 52 to increase the electrical signal being passed to data processor 56.

A first portion of the reflected light is collected by optical fibers 24b and conveyed in the device by optical fibers 24b for further mathematical processing. Incidentally, a second portion of fluorescent emission 34 is collected and conveyed with the first portion of reflected light. The second portion of fluorescent emission 34 and the first portion of the reflected light are conveyed through second optical transducer 48, in the form of a photodiode, which converts the optical light signal into an electrical signal. While it is an option to provide an optical filter to remove substantially all of the fluorescent emission prior to passing through second optical transducer 48, in the embodiment shown, neither the second portion of the fluorescent emission, nor the first portion of reflected light is filtered prior to their passing through second optical transducer 48, as these signals are used to measure the distance from the radiation source 22 to the surface of tooth 60. The unfiltered electrical signal is passed through second amplifier 54 to increase the electrical signal being passed to data processor 56.

Electronic parts that may be used in plaque detecting device 10 may include Taos TSL12S-LF photodiodes, Opamp Analog AD8544ARZ amplifiers, Semrock fluorescence filters (FF01-500-LP, FF01-475/64), and Atmel ATMEGA8L-8AU microprocessor.

Data processor 56 performs a mathematical manipulation on the inputs from first optical transducer 46 and second optical transducer 48. In the mathematical manipulation, the electrical signal resulting from filtered fluorescent emission 34 is modified to account for the electrical signal received from the unfiltered electrical signal that was used to determine distance from the tip of optical fiber 24b, i.e. the optical collector, to the surface of tooth 60. The relationship between the two signals is experimentally determined by measuring their respective signal strengths at known distances from the surface of objects coated with a fluorescent agent. The result of the mathematical manipulation is a corrected electrical signal which results in a compensated plaque value, as that term will be described and defined below.

FIG. 2 shows a plan view of a first embodiment of a plaque detecting device of the present invention. As shown, plaque detecting device 10 is in the form of a toothbrush with a handle portion 12 and a head portion 14. FIG. 2 shows the bristle face 16 of plaque detecting device 10. Bristle face 16 of head portion 14 is shown as generally oval in shape, but it is important that bristle face 16 may be in shapes such as triangle, square, rectangle, trapezoid, and other polygons, or circle, ellipse, crescent, deltoid, asteroid, or other curved shapes.

Radiation source 22, optical collectors and conveyors 24 and cleaning tufts 26 are located on bristle face 16. Radiation source 22, preferably in the form of a light emitter such as a light-emitting diode (LED), directs incident excitation radiation at the surfaces of the teeth to be cleaned. Optical collectors and conveyors 24, typically in the form of optical fibers, collect the fluorescent radiation emitted from the teeth. The optical fibers may be made of glasses such as silica, but may be made of other materials, such as fluorozirconate, fluoroaluminate, and chalcogenide glasses, but may also be in the form of plastic optical fibers (POFs).

Cleaning tufts 26 are made of approximately 20 to 50 individual bristles arranged on bristle face 16 in a manner to optimize cleaning of the surfaces of the teeth. FIG. 1 shows one arrangement of tufts 26 on bristle face 16. It is to be understood that the arrangement of tufts 26 on bristle face 16 is not limiting in the scope of the present invention. Typical tufts are approximately 0.063 inches (1.6 mm) in diameter, with a cross-sectional area of approximately 0.079 inches$^2$ (2 mm$^2$). The diameters of commonly used bristles are: 0.006 inch (0.15 mm) for soft bristles, 0.008 inch (0.2 mm) for medium bristles, and 0.010 inch (0.25 mm) for hard bristles.

A general problem in the recognition of caries, plaque or bacterial infection on teeth with the above-described method is found in that the detected fluorescent radiation can be disruptively superimposed with daylight or the artificial room lighting. This environmental light can likewise be reflected from the tooth 60 and thus collected by optical fibers 24a and 24b. The spectral region of the environmental light lying in the detection region in accordance with the invention results in a background signal, i.e. noise, which restricts the sensitivity of plaque detection.

This problem is effectively resolved in accordance with the invention in that the incident radiation 32 generated by radiation source 22 is periodically modulated. In this case, because of the short duration of the excited state the fluorescent emission 34 follows the intensity of the excitation radiation practically instantaneously. In contrast, the environmental light is not periodically modulated and is superimposed on the detected emission 34 solely as a constant component. For evaluation of the emission 34, now only the radiation modulated with the corresponding frequency is employed as detection signal and evaluated. In this way, the constant component of the environmental light is quasi-filtered out and plaque is detected virtually independently of the environmental light. Since the environmental light is, however, modulated slightly with the frequency of the mains voltage, there should be chosen as modulation frequency for the incident radiation 32 at a frequency which differs distinctively from the mains voltage frequency and preferably lies in the range between 100 Hz and 200 kHz.

The devices for detecting plaque in the oral cavity may also be used as part of, or in combination with, oral care systems which track the health of the oral cavity. Such systems can record plaque levels on teeth, gum, tongue, or cheek surfaces, before and after cleaning operations, as well as the track the plaque of levels over time, reporting the results to the user, or to dental care professionals.

The present invention may be better understood with reference to the following examples.

EXAMPLES

Example 1

Determination of the Compensated Plaque Value

A prototype plaque detecting toothbrush was created by modifying the head of a manual toothbrush by inserting a blue LED facing outwards from the head, allowing the light from the LED to illuminate the tooth surface. The LED was surrounded by an array of 12 fiber optic filaments, also pointed towards the tooth surface in the area illuminated by the blue LED. The fiber optics passed through the neck of the toothbrush to a pair of photo sensors (Taos TSL12S-LF) contained in the handle section of the toothbrush. The fibers were separated into two groups. One group passed through an optical filter (Semrock FF01-500/LP) that allowed only wavelengths above 515 nm to pass, while the second group allowed all wavelengths to pass, i.e. no optical filter was utilized. The filtered light represented the plaque value while the unfiltered light was used to interpret the distance between the optical collector, i.e. the tips of the optical fibers, and the surface of the tooth. The output of the photo sensors were connected to amplifiers (Analog devices AD8544ARZ) which in turn were connected to an 8 bit microcontroller (Atmel ATMEGA8L-8AU). The microcontroller contained two 10 bit analog to digital converters that allowed the information to be manipulated in a digital format within the microcontroller.

Using this apparatus, experiments were performed by using Typodent teeth models coated with a simulated plaque material containing a fluorescent material. The artificial plaque was painted onto the tooth surfaces in a way that approximated the manner in which plaque grows in the human mouth. The experiments consisted of positioning the optical collectors, e.g. the tips of fiber optic filaments, at varied distances from the tooth surface so as to enable a relationship to be created between the distance and the plaque value.

The prototype device was operated with the following set of parameters:
Sampling at 500 Hz (0.002 seconds), sequentially taking 4 measurements in repeating succession.
Averaging every 20 data points per output data value.
Prototype powered by 8-bit microcontroller @ 7 MHz clock speed.
RS232 readout of data to a spreadsheet, and
Ambient light compensation.

The prototype device was placed at distances between 0 and 10 mm from the surface of the model tooth surface. Readings were taken with Distance LED on, Distance LED off, Plaque LED on, and Plaque LED off. The value of the signals for Total Plaque and Total Distance were calculated at each distance using:

Total Plaque=Plaque LED on−Plaque LED off    (I)

Total Distance=Distance LED on−Distance LED off    (II)

Table I shows the measured/calculated values for Plaque LED on, Plaque LED off, Total Plaque, Distance LED on, Distance LED off, Total Distance.

The value of Column A (Total Plaque) was plotted against Column B (Total Distance). The resulting line was curve fitted to the follow straight line equation:

Total Plaque=1.304(Total Distance)−66.61    (III)

Since the value of Total Plaque at a distance of 1 mm from the surface of the model tooth surface was 226, a value of Compensated Plaque was determined using:

Compensated Plaque=226+(1.304(Total Distance)−66.61)/Total Plaque    (IV)

Table II shows the calculated values Compensated Plaque versus distance.

TABLE II

Compensated Plaque values as a function of distance for prototype oral cleaning device.

| Distance (mm) | Total Plaque A |
|---|---|
| 0 | 226.70 |
| 0.5 | 226.77 |
| 1.0 | 226.88 |
| 1.5 | 226.95 |
| 2.0 | 227.00 |
| 2.5 | 227.06 |
| 3.0 | 227.15 |
| 3.5 | 227.09 |
| 4.0 | 227.10 |
| 4.5 | 227.11 |
| 5.0 | 227.13 |
| 5.5 | 227.12 |
| 6.0 | 227.10 |
| 6.5 | 227.09 |
| 7.0 | 227.06 |
| 7.5 | 227.06 |
| 8.0 | 227.04 |
| 8.5 | 227.02 |
| 9.0 | 227.01 |
| 9.5 | 226.97 |
| 10.0 | 226.97 |
| AVERAGE | 227.02 |
| Std. Dev. | 0.12 |

TABLE I

Distance and Plaque readings from prototype oral cleaning device.

| Distance (mm) | Plaque LED On | Plaque LED Off | Total Plaque A | Distance LED On | Distance LED Off | Total Distance B |
|---|---|---|---|---|---|---|
| 0 | 331.48 | 125.26 | 206.22 | 242.74 | 80.30 | 162.44 |
| 0.5 | 356.15 | 129.00 | 227.15 | 268.80 | 83.15 | 185.65 |
| 1.0 | 355.63 | 129.53 | 226.10 | 285.68 | 81.84 | 203.84 |
| 1.5 | 345.75 | 126.58 | 219.17 | 291.42 | 80.96 | 210.46 |
| 2.0 | 337.68 | 128.27 | 209.41 | 295.05 | 82.95 | 212.10 |
| 2.5 | 327.62 | 127.24 | 200.38 | 295.38 | 81.05 | 214.33 |
| 3.0 | 316.36 | 127.87 | 188.49 | 287.32 | 81.91 | 205.41 |
| 3.5 | 300.70 | 122.00 | 178.70 | 278.04 | 77.11 | 200.93 |
| 4.0 | 296.38 | 127.90 | 168.48 | 275.14 | 81.41 | 193.73 |
| 4.5 | 277.42 | 120.84 | 156.58 | 260.42 | 76.53 | 183.89 |
| 5.0 | 273.38 | 128.21 | 145.17 | 257.83 | 81.04 | 176.79 |
| 5.5 | 220.13 | 83.10 | 137.03 | 223.33 | 54.00 | 169.33 |
| 6.0 | 258.05 | 128.67 | 129.38 | 242.81 | 82.48 | 160.33 |
| 6.5 | 249.26 | 127.68 | 121.58 | 233.68 | 81.00 | 152.68 |
| 7.0 | 241.89 | 128.50 | 113.39 | 225.61 | 82.33 | 143.28 |
| 7.5 | 236.22 | 129.06 | 107.16 | 219.78 | 81.61 | 138.17 |
| 8.0 | 230.22 | 129.44 | 100.78 | 212.61 | 81.56 | 131.05 |
| 8.5 | 225.94 | 129.59 | 96.35 | 208.47 | 82.24 | 126.23 |
| 9.0 | 216.50 | 128.35 | 88.15 | 200.35 | 81.40 | 118.95 |
| 9.5 | 214.35 | 129.00 | 85.35 | 195.95 | 81.80 | 114.15 |
| 10.0 | 212.87 | 131.33 | 81.54 | 194.47 | 82.93 | 111.53 |

The table shows the average calculated value of Compensated Plaque independent of distance is 227.02 with a standard deviation of 0.012 (0.05%). So, the value of the plaque reading has been compensated for, taking into account the distance from the optical collector to the surface of the model tooth.

What is claimed is:

1. A method for detecting plaque in the oral cavity, said method comprising:
   contacting a surface of said oral cavity with incident radiation, said surface comprising applied thereto a fluorescent agent capable of binding to plaque, whereby said contact provides reflected light having a first wavelength and a fluorescent emission emanating from said fluorescent agent having a second wavelength,
   collecting and conveying a first portion of said fluorescent emission resulting from said contact to a first means for converting an optical signal of said first fluorescent emission to an electrical signal of said first portion of fluorescent emission and converting said optical signal of said first portion of fluorescent emission to said electrical signal of said first portion of said fluorescent emission,
   collecting and conveying a first portion of said reflected light to a second means for converting an optical signal of said first portion of said reflected light to an electrical signal of said first portion of said reflected light and converting said optical signal of said first portion of said reflected light to said electrical signal of said first portion of said reflected light; and
   mathematically manipulating said electrical signal of said first portion of said fluorescent emission and said first portion of said reflected light to provide a compensated plaque value.

2. The method of claim 1 wherein said fluorescent agent comprises fluorescein or a salt thereof and said incident radiation has a peak wavelength of from about 450 to about 500 nanometers.

3. The method of claim 2 wherein said incident radiation is passed through a first optical filter prior to contact with said surface.

4. The method of claim 3 wherein said incident radiation has a wavelength of about 470 nanometers.

5. The method of claim 1 wherein a second portion of said reflected light is simultaneously collected and conveyed with said first portion of said fluorescent emission through a second optical filter prior to conversion of said optical signal of said fluorescent emission to said electrical signal of said fluorescent emission, said second filter removing light having a wavelength of below about 515 nanometers.

6. The method of claim 1 wherein said electrical signal of said fluorescent emission and said reflected light are amplified prior to said mathematical manipulation.

7. The method of claim 1 wherein said electrical signal of said fluorescent emission and said reflected light are converted to a digital format prior to said mathematical manipulation.

8. The method of claim 1 wherein a second portion of said fluorescent emission is simultaneously conveyed with said first portion of said reflected light.

9. The method of claim 1 wherein said conveyance of said first portions of said fluorescent emission and reflected light is substantially simultaneous.

10. The method of claim 1 wherein said fluorescent emission comprises a peak wavelength of from about 520 to about 530 nanometers.

11. The method of claim 1 wherein said reflected light and said fluorescent emission are collected and conveyed by optical fibers.

12. The method of claim 7 wherein said first portion of said reflected light is simultaneously conveyed with said second portion of said fluorescent emission through a third optical filter prior to conversion of said optical signal of said fluorescent emission to said electrical signal of said fluorescent emission, said third filter removing light having a wavelength of above about 515 nanometers.

13. The method of claim 1 wherein said compensated plaque value is determined as a function of the distance between said point of collection of said fluorescent emission and said surface of said oral cavity.

14. A device for detecting plaque on a surface of the oral cavity, said device comprising:
   a radiation source for directing incident radiation onto said surface of said oral cavity,
   optical collectors for collecting reflected light and fluorescent emission,
   optical pathways for conveying said collected reflected light and said collected fluorescent emission in said device,
   means for converting an optical light signal of said reflected light and said fluorescent emission to an electrical signal; and
   means for mathematically manipulating said electrical signal of said reflected light and said fluorescent emission to determine a compensated plaque value.

15. The device of claim 14 wherein said optical collectors comprise an optical fiber.

16. The device of claim 14 wherein said optical pathway comprises an optical fiber.

17. The device of claim 15 wherein said optical pathway comprises said optical fiber.

18. The device of claim 14 wherein said means for converting said optical light signal of said reflected light and fluorescent emission to said electrical signal comprises an optical transducer.

19. The device of claim 14 further comprising means for amplifying or conditioning said electrical signal of said reflected light and said fluorescent emission.

20. The device of claim 14 further comprising a first optical filter through which said incident radiation is passed prior to contact with said surface.

21. The device of claim 14 further comprising a second optical filter through which a second portion of said reflected light and a first portion of said fluorescent emission is conveyed prior to conversion of said optical light signal to said electrical signal.

22. The device of claim 14 further comprising a third optical filter through which a first portion of said reflected light and a second portion of said fluorescent emission is conveyed prior to conversion of said optical light signal to said electrical signal.

23. The device of claim 14 wherein said means for mathematically manipulating said electrical signal of said reflected light and said fluorescent emission comprises a data processor, said data processor further comprising an analogue-to-digital converter for converting said electrical signal of said reflective light and said fluorescent emission from an analogue format to a digital format prior to manipulation of said electrical signal.

* * * * *